United States Patent [19]

Amano et al.

[11] Patent Number: 5,032,523

[45] Date of Patent: Jul. 16, 1991

[54] PREPARATION OF OPTICALLY ACTIVE ESTERS

[75] Inventors: Masaki Amano, Kashiwa; Haruhiko Toda, Chiba; Minako Yasu, Shibuya; Toshiyuki Koyagi, Kawasaki, all of Japan

[73] Assignee: Lion Corporation, Tokyo, Japan

[21] Appl. No.: 143,023

[22] Filed: Jan. 12, 1988

[30] Foreign Application Priority Data

Jan. 14, 1987 [JP] Japan .................................. 62-6750
Oct. 6, 1987 [JP] Japan .............................. 62-251876
Dec. 14, 1987 [JP] Japan .............................. 62-316564

[51] Int. Cl.$^5$ ............................................. C12P 7/62
[52] U.S. Cl. ..................................... 435/280; 435/135
[58] Field of Search ............................... 435/135, 280

[56] References Cited

U.S. PATENT DOCUMENTS 4,601,987 7/1986 Klibanov et al. .
4,719,178 1/1988 Macrae .............................. 435/135

FOREIGN PATENT DOCUMENTS 60-78596 5/1985 Japan .
62-19090 1/1987 Japan .

OTHER PUBLICATIONS

Cambou et al.—Chem. Abst., vol. 102, (1985), p. 145631r.
Bello et al.—Chem. Abst., vol. 105, (1986), p. 222,110m.
Lazar—Chem. Abst., vol. 104, (1986), p. 32969e.
Yamane—Chem. Abst., vol. 102, (1985), p. 44263s.
Nakanishi et al.—Chem. Abst., vol. 103, (1985), p. 21136j.
B. Cambou and A. M. Klobanov, "Unusual Catalytic Properties of Usual Enzymes", *Annals New York Academy of Sciences*, 434, (1984), pp. 219–223.

*Primary Examiner*—Sam Rosen
*Attorney, Agent, or Firm*—Wegner, Cantor, Mueller & Player

[57] ABSTRACT

A process for separating an optically active substanbce comprising the steps of:
(a) effecting a transesterification reaction between an ester of a linear or branched aliphatic racemic alcohol and an alcohol in an organic solvent containing an enzyme suspended therein; and
(b) separating an optically active compound from the resultant reaction mixture.

12 Claims, No Drawings

PREPARATION OF OPTICALLY ACTIVE ESTERS

BACKGROUND OF THE INVENTION

1. Field of the Invention

The present invention relates to a preparation of an optically active substance having a physiological activity. More specifically, it relates to an enzymatic preparation of an intermediate for synthesizing an optically active substance (e.g., epihalohydrin), i.e., a so-called "chiral synthon", capable of reducing the synthesis steps of the optically active substance. The present invention also relates to a bioreactor system suitable for use in an enzymatic preparation of an optically active substance useful as an important intermediate for synthesis of, for example, pharmaceutical products using a powdered or granulate enzyme in an organic solvent.

2. Description of the Related Art

Optically active pharmaceutical products have been heretofore produced by fermentation (enzyme) methods using microorganisms (enzymes), pure organic synthesis methods, or combination of the above-mentioned two methods. Of these methods, when non-natural type pharmaceutical products are produced, the organic synthesis methods or the combined methods are generally used. According to the organic synthesis methods, optically active pharmaceutical products having structures completely different from those of natural products can be prepared and, according to the combined methods, optically active pharmaceutical products having structures similar to those of natural products can be prepared.

The above-mentioned organic synthesis methods can advantageously prepare new types of pharmaceutical products having completely different new structures. However, there are disadvantages in these methods that the starting materials are relatively expensive optically active natural sugars or amino acids and that the synthesis steps or routes are generally long.

On the other hand, recently, effective syntheses of optically active synthetic intermediates (i.e., chiral synthons) to reduce the synthesis steps or routes of the organic synthesis methods are noted. Of these chiral synthon, β-blocker synthesis intermediates such as (R)-solketal and optically active epoxides are commercially available. For example,

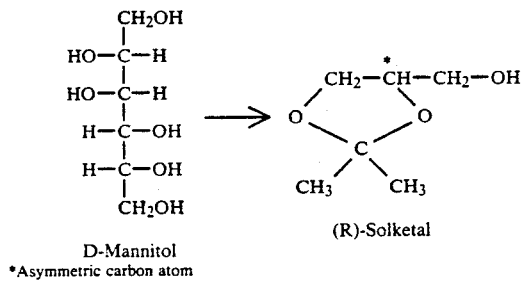

D-Mannitol → (R)-Solketal
*Asymmetric carbon atom

However, according to these methods, the optically active intermediates are only derived from optically active natural products such as sugars and amino acids and new synthesis methods for chiral synthon have not been developed.

Recently, Iriuchijima, Hamaguchi et. al. reported an effective enzymatic synthesis of glycerol derivatives, which are chiral synthon of β-blocker, i.e., an arrhythmia agent in Agric. Biol. Chem., 46, 1153 (1982) and Agric. Biol. Chem., 50, 1629 (1986). However, since enzymes dissolved in water are used in these experiments, it is difficult to recover and reutilize these enzymes. On the other hand, A. M. Klibanov reported the preparation of optically active esters or alcohols in J. Am. Chem. Soc., 107, 7072 (1985) by using a racemic alcohol as a starting material, a solid enzyme suspended in an organic solvent, and an esterified alcohol. However, it is reported that, in this method, a secondary alcohol is used as a racemic alcohol and that, when a primary alcohol is used, the desired product having a high optical purity cannot be obtained and no specific examples are given in this reference.

Furthermore, the following methods are reported as the synthesis methods of optically active epihalohydrins.

① Synthesis from D-mannitol (J. J. Baldwin, J. Org. Chem., 43, 4876, (1978))

According to this method, (S)- and (R)-epichlorohydrins are synthesized from D-mannitol. However, this method is disadvantageous in that the synthesis route is long and the use of heavy metal compounds such as lead tetraacetate causes safety problems.

② Synthesis from optically active 2,3-dichloro-1-propanol (JP-A-62-6697)

(R)-2,3-dichloro-1-propanol is removed from the racemic mixture thereof by utilizing the same with an immobilized microorganism and the resultant (S)-2,3-dichloro-1-propanol is treated with a two-layer solution of ether/aqueous NaOH solution, followed by cyclization to obtain (R)-epichlorohydrin. However, this method is disadvantageous in that a cumbersome immobilizing treatment of a microorganism, sterilization of the reaction apparatus and the like are required and that the synthesis of (S)-epichlorohydrin is impossible.

③ A method in which starting materials and enzymes similar to those of the present invention are used (Shigeki Hamaguchi; Text of the 22nd Biochemical Engineering Lecture Course, page 41, (1987))

Although this method proposes the use of starting materials and enzymes similar to those of the present invention, the recovery and reutilization of enzymes and the attainment of the continuous reaction are impossible because of the aqueous reaction, and because cumbersome post-treatments such as extraction are required. Furthermore, during the enzymatic hydrolysis reaction, free acids are generated and cause non-enzymatic (i.e., non-stereoselective) hydrolysis. Thus, since the optical purity of the desired products, (S)-alcohols or (R)-esters is decreased, the reaction must be carried out while the generating acid is neutralized with an aqueous NaOH solution. Furthermore, since the starting racemic esters have a low solubility in water, the increase in the reaction temperature and the addition of an organic solvent are required to accelerate the hydrolysis reaction. These actions, however, can deactivate the enzymes.

In addition, after the enzymatic hydrolysis reaction, although the desired (R)-esters and (S)-alcohols can be obtained by extraction, recovery and reutilization of enzymes used is extremely difficult because of the aqueous reaction.

Moreover, according to this method, the resultant mixture of (R)-ester and (S)-alcohol is directly treated, without separation, with an aqueous NaOH solution having a pH of 12, whereby only the (S)-alcohol is cyclized to form (S)-epichlorohydrin and the (R)-ester is recovered. The recovery of (R)-ester and (S)-epichlorohydrin should be carried out by extraction.

Heretofore, various methods for obtaining optically active substance have been known. Examples of such methods are (a) optical resolution of racemic mixtures by enzymes and microorganisms, (b) optical resolution of racemic mixtures by chemical methods, (c) methods for deriving optically active substances from optically active natural products, (d) asymmetric syntheses by enzymes and microorganisms, and (e) asymmetric syntheses by chemical methods. Of these methods, the methods (a) and (d) using biocatalysts such as enzymes and microorganisms have generally become noted as the best methods for practical use because of mild reaction conditions and a high selectivity.

For example, the above-mentioned method (a) using a bioreactor is commercially utilized in the production of optically active amino acids, i.e., racemic acylamino acids are hydrolyzed by reaction kinetics optical resolution using enzymes, whereby the enantiomer is optically resoluted. According to this method, immobilized enzymes bonded to DEAE-Sephadex by a carrier bonding method are used. However, since this reaction is carried out in an aqueous medium, a problem arises in that hydrophobic substrates are not easy to treat (Chibata et. al., Agr. Biol. Chem., 33 (7), 1047–1052, 1969). Furthermore, this method has a problem in that the retentionability of enzyme activity is low. For example, the enzyme activity in a fixed bed type reactor is decreased by 60% in 32 days.

The above-mentioned method (d) is also practically used in the commercial production of L-asparginic acid or L-malic acid in a bioreactor using an immobilized enzyme. This reaction is also carried out in an aqueous medium (Chibata et. al., Appl. Microbiol. 27, 878, 1974). Furthermore, since this method uses, as an immobilization method, a gel-entrapment immobilization method in which polyacrylamide or copper carageenan is used, the immobilization operation is complicated and, since the reaction is carried out in an aqueous medium, the reaction of hydrophobic substrates is difficult.

Furthermore, a research report of the above-mentioned method (a) using both water and organic solvents has been proposed in Asada et. al., JP-A-60-78596. According to this method, racemic compounds are optically resolved by hydrolases. However, this method has disadvantages from the practical viewpoint in that a complicated immobilization treatment of enzymes is required and that, since water and an organic solvent must be alternately used, the operations are complicated and the process control is difficult.

Recently, it has been recognized in the art that an organic solvent type bioreactor capable of increasing the reactivity by solubilizing hydrophobic substrates is necessary. Various studies have been made to develop such a bioreactor. For example, methods using immobilized enzymes (i.e., ion bonding method+crosslinking method) (see Matsuno et. al., Bio/Technology, 3, 459, 1985) or methods for separating enzymes from hydrophobic products and for effecting the reactions at the interfaces of micro-pores of thin membranes by using micropore thin membranes (e.g., precision filter membranes) (see Yamane et. al., Yu Kagaku, 33, 683, 1984).

According to Matsuno et. al. method, the enzymes are likely to be deactivated when immobilized, especially when crosslinked with glutaric aldehyde and, furthermore, extensive work and time are required for the immobilization operation. On the other hand, according to Yamane et. al. method, the reactivity largely depends upon the water content of glycerol solution. For example, the maximum reactivity can be obtained at the water content of 3 to 4% and the reactivity is decreased either below or above this water content. In addition, according to this ester synthesis reaction, since water is always formed, it is very difficult to maintain the water content in the system and, furthermore, complicated reactors are required. Thus, this method is not suitable for practical use.

As bioreactors for enzymatic reactions, two types, i.e., homogeneous phase type bioreactors in which enzymes are solubilized in aqueous media and two phase type bioreactors in which enzymes are used in the immobilized state, have been heretofore used. Of these bioreactors, the homogeneous bioreactors include, for example, agitating vessel type bioreactors and ultrafiltration membrane type reactors. However, these bioreactors, especially except for those using ultrafiltration membrane, have disadvantages in that, since catalytic enzymes flow out from the vessels, the continuous reaction advantageous for the commercialization cannot be readily realized.

The two-phase type bioreactors generally use immobilized enzymes and include, for example, the agitating vessel type, fixed or packed bed type, fluidized bed type, membrane type, and suspension air bubbling column type reactors, all of which can be used in a continuation reaction system.

As catalysts for bioreactors, various kinds of substances other than purified enzymes have been recently used. That is, in the case of, for example, intracellular enzymes, which are difficult to isolate, "treated cells" obtained by treating the same by heat, organic solvents, or surfactants to retain only the property capable of catalyzing the desired reaction can be used. "Pausing or resting cells", which are living cells but do not proliferate or "proliferating cells" capable of proliferating in the reactor, can also be used. These enzymes can be used not only in a one step reaction but also in a multi-step reaction.

As immobilization methods for insolubilizing enzymes in water, various methods including a carrier bonding method, a crosslinking method, and a gel-entrapment method are known. However, these methods generally require a complicated treating method and enzymes sometimes are deactivated to cause a decrease in the activity of the enzymes. In the case of the gel-entrapment methods and the like, the permeability of substrates and products into polymeric substances surrounding the enzymes is low and, therefore, the reactivity is unpreferably decreased. On the other hand, in the case of the physical adsorption methods (carrier bonding methods), in which the enzymes are adsorbed on the surface of inorganic carriers or polymeric substances, the interaction between the enzyme and the carrier is weak and, therefore, the adsorbed enzyme is sometimes eliminated from the surface of the carrier. Thus, these methods are disadvantageous for the continuous reaction in an aqueous solution.

Furthermore, regarding the reaction solvents, the use of an organic solvent has gradually increased, in addition to the conventional aqueous solution, and it is recognized that (immobilized) enzymes microorganisms are relatively stable even in organic solvents. Examples of these proposals are the use of powdered enzymes in organic solvents for a production of diglycerides from the ester synthesis reaction of glycerol and fatty acids (JP-A-62-19090) and the use of powdered enzymes in organic solvents for synthesis of optically active substances in batchwise reactions (Klibanov et. al., J. Am. Chem. Soc., 107, 7072, 1985). However, although the enzymes can be recovered by filtration and can be repeatedly used, there are various problems in the practical use thereof in commercial production because of, for example, the cumbersome filtration operation and fluctuations in the reactivity caused by a difficulty in control of the water content in the enzymes when repeatedly used.

SUMMARY OF THE INVENTION

Accordingly, the objects of the present invention are to eliminate the above-mentioned problems in the prior art and to provide a method for optically resolving an optically active substance (or optical antipode) effectively from a transesterification reaction product of an ester of linear or branched aliphatic racemic alcohol (i.e., "the racemic ester" hereinbelow) in the presence of an enzyme and to improve the recovery and reutilization of the enzyme.

Another object of the present invention is to provide a process for commercially advantageously preparing an optically active epihalohydrin with a simple operation and having an excellent enzymes recovery and reutilization capability.

A further object of the present invention is to provide an organic solvent type bioreactor system capable of effectively carrying out optical resolution or asymmetric synthesis and capable of stably using an enzyme as a catalyst for a long time without using a cumbersome immobilizing treatment such as a crosslinking method and a gel-entrapment method and without using a complicated ultrafiltration membrane or precision filtration membrane apparatus.

Other objects and the advantages of the present invention will be apparent from the following description.

In accordance with the present invention, there is provided a process for separating an optically active substance comprising the steps of:

(a) effecting a transesterification reaction between an ester of a linear or branched aliphatic racemic alcohol and an alcohol in an organic solvent containing an enzyme suspended therein; and (b) separating an optically active compound from the resultant reaction mixture.

In accordance with the present invention, there is also provided a process for preparing an optically active epihalohydrin comprising the steps of:

(1) enzymatic alcohol addition decomposing a racemic product (III) of 3-halo-2-acyloxy-1-alkyl- or arylsulfonyloxy propane in an organic solvent containing an enzyme suspended therein to prepare a reaction product mixture containing (S)-alcohol (IV) and the corresponding (R)-ester (V) (i.e., step 1);

(2) removing the enzyme from the reaction product mixture by filtration, followed by treating the reaction product mixture with an organic solvent-aqueous, alkaline two layer system to obtain (S)-epihalohydrin (VI) (i.e., step 2); and (3) distilling off the (S)-epihalohydrin (VI) from the organic layer, followed by treating (R) ester (V) contained in the residue with alkali to obtain (R)-epihalohydrin (VII) (i.e., step 3).

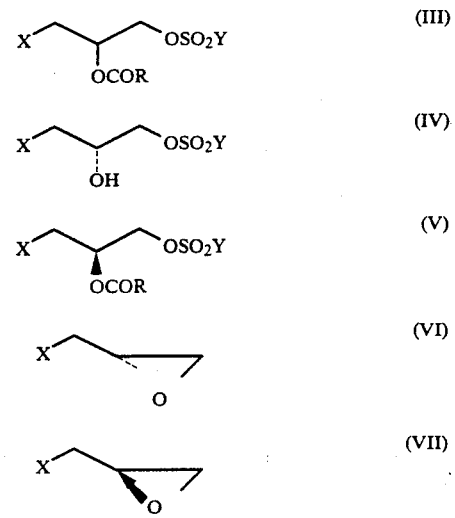

wherein X represents halogen, R represents aliphatic hydrocarbon residue having 1 to 8 carbon atoms, and Y represents an aromatic hydrocarbon residue, an aromatic hydrocarbon residue substituted with $C_1$–$C_4$ alkyl group, an aliphatic hydrocarbon residue having 1 to 8 carbon atoms, or a halogen substituted residue thereof.

These steps can be summarized as follows.

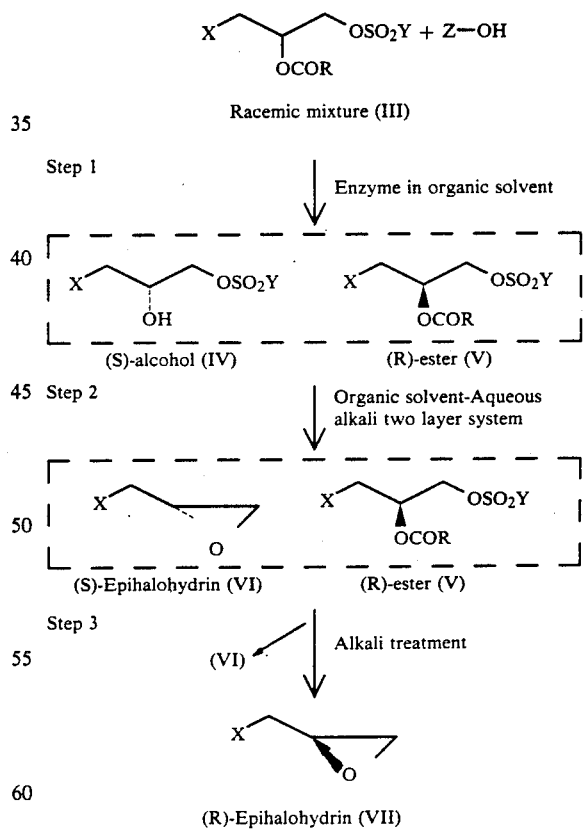

wherein X, R, and Y are as defined above and Z represents an alcohol residue.

Thus, according to the second aspect of the present invention, to improve the recovery and reutilization capabilities of the enzyme, non-aqueous organic solvents which do not dissolve the enzymes are selected and, to effectively carry out the optical resolution, the racemic mixture of 3-halo-2-acyloxy-1-alkyl (or aryl) sulfonyloxy propane is used as a starting substance in transesterification reaction and the alcohol addition decomposition reaction of the racemic mixture is selected.

In accordance with the present invention, there is further provided an organic solvent type bioreactor system wherein a nucleophilic agent comprising an organic solvent containing at least one reaction substrate selected from the group consisting of (a) esters of racemic alcohols, (b) diesters of prochiral type symmetric diols, and (c) diesters of metho type diols and an alcohol is used as a moving bed and is introduced into a fixed bed containing a hydrolase (i.e., a hydrolysis enzyme) to effect an alcohol addition decomposition.

DESCRIPTION OF THE PREFERRED EMBODIMENT

According to the present invention, a non-aqueous organic solvent which does not dissolve an enzyme is selected as a reaction solvent to improve the recovery and reutilization of the enzyme and the alcohol addition decomposition reaction (i.e., alcoholysis) of racemic esters in the transesterification reaction is selected as a reaction capable of effectively carrying out the optical resolution. The Klibanov reaction corresponds to the esterification reaction of racemic alcohol in the transesterification reaction.

The reaction schemes of the present invention and the Klibanov reaction are as follows:

Present Invention

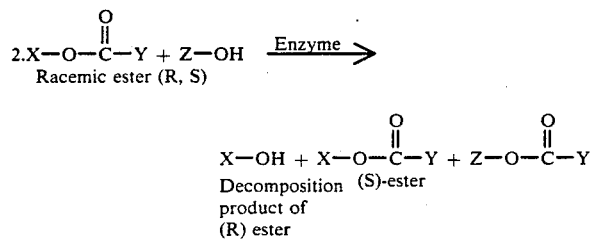

Klibanov's Reaction

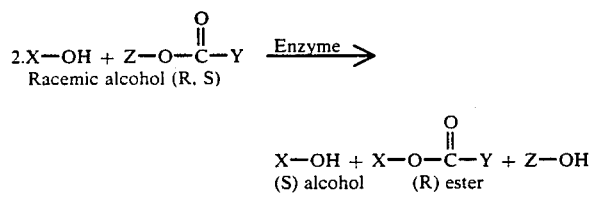

The racemic esters usable as a starting material are those having a basic skeleton represented by the following formula (I) or (II).

$$
\begin{array}{c}
R^1 \quad R^4 \quad R^6 \quad O \\
| \quad\quad | \quad\quad | \quad\quad \| \\
R^2-C^3-C^2-C^1-O-C-R, \\
| \quad\quad | \quad\quad | \\
R^3 \quad R^5 \quad R^7
\end{array}
\tag{I}
$$

Ester of Primary Alcohol or $$
\begin{array}{c}
R^1 \quad R^4 \quad R^5 \\
| \quad\quad | \quad\quad | \\
R^2-C^3-C^2-C^1-R^6 \\
| \quad\quad | \quad\quad | \\
R^3 \quad O \quad R^7 \\
\quad\quad | \\
\quad\quad O=C-R
\end{array}
\tag{II}
$$

Ester of Secondary Alcohol wherein $R^1$ to $R^7$ independently represents a functional group containing at least one atom selected from the group consisting of hydrogen, carbon, halogen, oxygen, nitrogen, sulfur, and phosphorus, R is an aliphatic hydrocarbon residue having 1 to 8 carbon atoms as previously defined, and the asymmetric carbon is present only at $C^2$ position and the carbon atoms $C^1$ and $C^3$ are not asymmetric. That is, in the formula (I), at least two groups of $R^1$ to $R^3$ are the same functional group and $R^6$ and $R^7$ are the same functional groups and, in the formula (II), at least two groups of $R^1$ to $R^3$ are the same groups and at least two groups of $R^5$ to $R^7$ are the same group.

In the preparation of the optically active epihalohydrin, the racemic ester having the above-mentioned formula (III) is used as a starting material. Examples of such esters are esters of secondary alcohols such as 3-chloro-2-acetoxy-1-p-toluene sulfonyloxy propane.

The alcohols (Z-OH) usable in the present invention are those having no asymmetric carbon atoms, racemic alcohols having at least one asymmetric carbon, or optically active alcohols.

More specifically, examples of the alcohols having no asymmetric carbon atoms are linear or branched aliphatic alcohols having 1 to 10 carbon atoms, especially linear or branched aliphatic alcohols having 3 to 8 carbon atoms, such as propanol, butanol, pentanol, octanol, isopropanol, isobutanol. Examples of the racemic alcohols having asymmetric carbon are linear or branched aliphatic alcohols having 1 to 10 carbon atoms such as racemic 2-butanol, racemic methylisopropylcarbinol and alcohols having at least one aromatic ring with 6 to 10 carbon atoms such as racemic 1-phenylethanol, racemic 1-phenylpropanol. Furthermore, examples of the optically active alcohols are linear or branched aliphatic alcohols having 1 to 10 carbon atoms such as (R)-2-butanol, (S)-2-butanol, (R)-methylisopropylcarbinol, (S)-methylisopropylcarbinol and alcohols having at least one aromatic ring with 6 to 10 carbon atoms such as (R)-1-phenylethanol, (S)-1-phenylethanol, (R)-1-phenylpropanol, (S)-1-phenylpropanol. When the racemic alcohols or the optically active alcohols are used, the chemical structure of the alcohol should be different from the alcohol moiety of the racemic alcohol ester of the present invention.

The organic solvents usable in the present invention are the above-mentioned alcohols and the other non-aqueous organic solvents capable of suspending the enzymes therein. Examples of such non-aqueous organic solvent are linear type hydrocarbons such as n-pentane, n-hexane, and n-heptane; branched type hydrocarbons such as isobutane, isopentane, and 2-methylpentane; aliphatic hydrocarbons such as cyclopentane and cyclohexane; halogenated hydrocarbons such as methylene dichloride, chloroform, carbon tetrachloride, dichloroethane, and trichloroethane; aromatic hydrocarbons such as benzene, toluene, and xylene; aliphatic ethers such as diethyl ether, diisopropyl ether and n-dibutyl ether; and alicyclic ethers such as tetrahydrofuran and tetrahydropyran. Of these non-aqueous organic solvents, n-hexane, toluene, diethyl ether, diisopropyl ether, n-dibutyl ether, carbon tetrachloride, and methylene dichloride are preferably used.

The enzymes usable in the present invention are hydrolases. Examples of such enzymes are lipases such as lipases derived from swine pancreas, lipases derived from yeast belonging to genus Candida, and lipases derived from microorganisms belonging to genus Aspergillus, Mucor and Pseudomonas, esterases derived from swine liver, and proteinases such as, trypsin, chymotrypsin, and subtilisin.

The transesterification reaction according to the present invention means the alcohol addition decomposition reaction, i.e., the reaction in which the above-mentioned racemic esters are decomposed, in the presence of the above-mentioned enzymes, by the above-mentioned alcohols. Schemes of one of the typical reactions are as follows:

(A) In the case of alcohol (Z-OH) having no asymmetric carbon atom

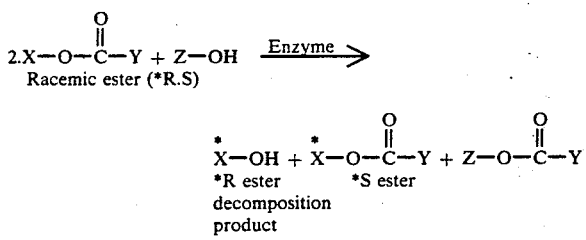

(B) In the case of racemic alcohol (Z-OH)

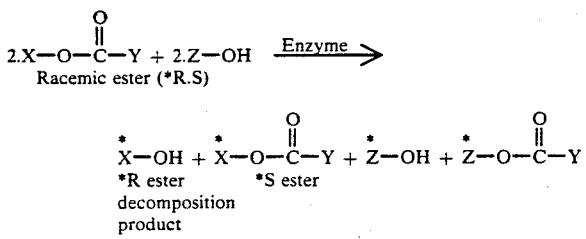

(C) In the case of optically active alcohol (Z-OH)

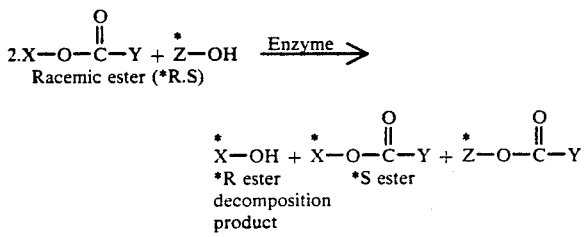

wherein * represents optically active substance, R.S represents racemic mixture (or product), *R represents enantiomer of absolute configuration R, and *S represents enantiomer of absolute configuration S. In the present invention and in the Klibanov reaction, the necessary components in the reaction mixture are alcohols (X-OH) and esters (XO-OCY).

After the enzymatic reactions, the optically active substances are separated from the resultant reaction mixture, and thus the esters (XO-OCY) or the alcohols (X-OH) are separated from the reaction system with a high purity. Typical separation methods include, for example, extraction operations with a two phase system of water-insoluble or slightly water-soluble organic solvents and water, column separation operation, and separation by distillation.

In the practice of the present invention, the water content of the reaction system should be extremely small, preferably under substantially non-aqueous conditions. Typically, the water content in the liquid phase, racemic esters, alcohols, and non-aqueous organic solvent is preferably 2% (W/V) or less, more preferably 0.5% (W/V) or less.

In the case of epihalohydrin preparation, the reaction mixture obtained by recovering the enzyme by filtration after the enzymatic reaction can be isolated as the (R)-ester (V) and the (S)-alcohol (IV), both having a high optical purity. However, when these compounds are converted to each epihalohydrin having a different steric configuration, the reaction mixture after removing the enzyme can be directly alkali treated to obtain the (S)-epihalohydrin (VI). In this step, the (S)-alcohol (IV) is preferably cyclized in a two phase system of organic solvent/aqueous alkaline solution, in view of the reaction selectivity, the prevention of racemization, and the easy separation of the resultant products. The alkali concentration is preferably 0.5 to 1.5N solution, more practically about 1N solution and the reaction temperature is practically 50° C. or less as the organic solvent, the solvent used in the first transesterification reaction, can be used. The preferable organic solvents in this step are those having a large boiling point difference with the epihalohydrin. Typical examples of the aqueous alkaline solution are aqueous solutions of NaOH, KOH, NaHCO$_3$, and Na$_2$CO$_3$. Practically, an aqueous NaOH solution is preferably used.

The typical weight ratio of the organic solvent/the aqueous alkaline solution is 0.1–10/1, more preferably 0.5–2/1.

In the following step 3, the (S)-epihalohydrin (VI) is distilled-off and recovered and the resultant (R)-ester (V) is alkali treated to obtain the (R)-epihalohydrin (VII). As the alkali reagent, NaOMe, NaOEt, KOMe, t-BuOK, KOH, and NaOH are preferably used.

The mechanism of the separation of the optically active substances by the enzymatic transesterification reaction of the racemic alcohols according to the present invention is believed to be as follows.

When no enzymes are added to the reaction systems according to the present invention, the intended transesterification reactions between the racemic esters and the alcohols do not occur during the time of the batch reactions shown in the examples as long as the occurrence of the reaction is confirmed by a gas chromatography or a high performance liquid chromatography. Accordingly, it is clear that the enzymes act as a catalyst for the reaction. Furthermore, it is estimated from the Klibanov report (i.e., the transesterification reaction does not occur at all, when the enzyme activity of lipase is completely deactivated by p-nitrophenyl diethyl phosphate) that the desired reaction does not occur according to the nucleophilicity of the enzyme protein. Thus, it is believed that the reaction occurs at the active centers of the enzymes.

As shown in the above-mentioned reaction scheme, since *R-esters in the racemic esters are preferentially reacted with the alcohol (Z-OH) to form the hydrolysates (X-OH) and since the *S-esters remain in the reaction system without undergoing to the transesterification reaction, the mechanism of the present reaction will be estimated in either of the following three instances.

(1) When the enzymes form complexes with the substrate, i.e., the racemic esters, the *R esters easily form the complexes and the *S esters do not easily form the complexes. Accordingly, since the *R esters readily react with but the *S esters do not readily react with the alcohol, the alcohols X-OH, i.e., the hydrolysate of the *R esters and the unreacted *S rich esters are contained in the final products.

(2) The formability of the complexes between the enzyme and the racemic esters is assumed to be substantially the same. However, when the reaction rate of the transesterification reaction of the complexes with the alcohol (Z-OH) in the reaction system extremely large in the case of the complexes of the enzymes with the *R esters when compared to those of the complexes of the enzymes with the *S esters the final products contain the alcohol derived from the hydrolysis of the R-ester and the *S-esters are contained.

(3) According to the combination effects of the above-mentioned cases (1) and (2), i.e., as a result of the combination of the difference in the formability of the complex of the enzyme with the *R ester and the *S ester and the difference in the reactability of the transesterification reaction of each complex with the alcohol (Z-OH), the above-mentioned results can be obtained.

According to the third aspect of the present invention, the organic solvent type bioreactors are capable of continuously preparing optically active alcohols or their derivatives such as optically active esters and monoesters. Thus, (a) optional resolution of esters of racemic alcohols by alcoholysis, (b) alcoholysis of diesters of prochiral type symmetric diols, and (c) asymmetric synthesis by alcoholysis of diesters of metho type diols can be continuously carried out by the same bioreactor system according to the present invention.

Typical examples of such reactions are as follows.

Optical Resolution

2R'OCR" + Z'OH → *R'OH + *ROCR" + Z'OCR"
‖                      ‖           ‖
O                      O           O

Ester of Racemic      Optically    Ester of
Alcohol               Active       Optically
                      Alcohol      Active
                                   Alcohol Asymmetric Synthesis

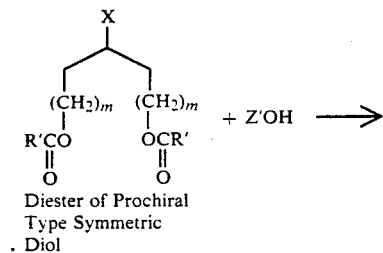
Diester of Prochiral
Type Symmetric
Diol

+ Z'OH →

-continued

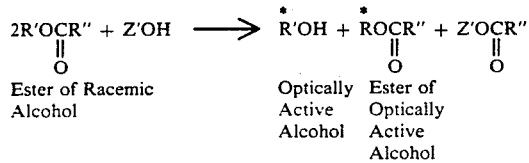
Optically
Active
Monoester

+ Z'OCR'
‖
O

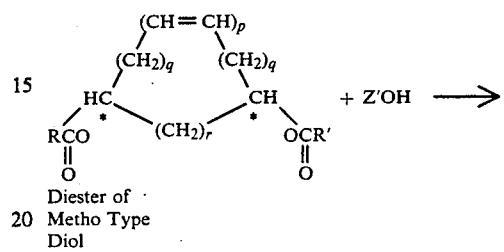
Diester of
Metho Type
Diol

+ Z'OH →

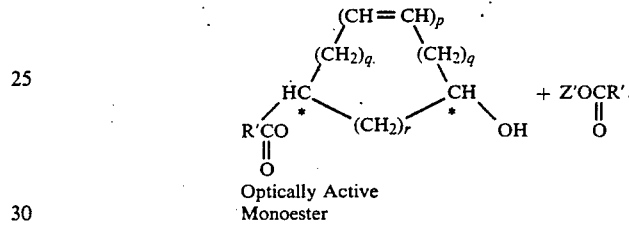
Optically Active
Monoester

+ Z'OCR'
‖
O wherein R' and R" independently represent substituted or unsubstituted aliphatic hydrocarbon residue or substituted or unsubstituted aromatic hydrocarbon residue, $m=0-5$, $p=0-2$, $q=0-5$, $r=0-5$, * represents optically active carbon atom, X represents hydrogen, halogen, substituted or unsubstituted aliphatic hydrocarbon residue, substituted or unsubstituted aromatic hydrocarbon residue, or at least one substituent including heteroatom such as oxygen, nitrogen, sulfur.

The types of the bioreactors according to the present invention may be any conventional solid-liquid two phase type including an agitating vessel type, fixed or packed layer type, fluidized bed type, membrane type, and suspension air bubbling column type, so long as organic solvents are used as the liquid. These types of solid-liquid two phase systems are conventionally used for immobilized enzymes·microorganisms and some free microorganisms. Especially, in view of the reaction efficiency and the retentionability of enzymes·microorganisms in the fixed phase, fixed or packed layer type reactors in which the enzymes·microorganisms are packed in the column and through which substrates and alcohols can be upwardly or downwardly passed, are used.

Furthermore, as a preferable bioreactor system for actual industrial production, an organic solvent containing a reactive substrate, one component of the mobile phase is fed from one reservoir, while the nucleophilic reagent, an alcohol or an organic solvent containing alcohol, is separately fed from the other reservoir. Thus, both are mixed together immediately before feeding to the fixed layer and the desired alcoholysis is effected by an enzymatic reaction in the fixed layer. According to this system, since non-sterically selective alcoholysis is suppressed, the desired continuous production of optically active substances having a high purity can be attained.

Examples of the reaction substrates usable in the mobile phase are (a) esters of racemic alcohols such as esters of primary and secondary alcohols, e.g., solketal butyrate, 2,3-dichloro-1-propanol butyrate, and 3-chloro-2-acetoxy-1-p-toluene sulfonyloxypropane; (b) diesters of prochiral type symmetric diols such as 2-phenyl-1,3-diacetoxy propane; and (c) diesters of metho type diols such as cis-1,4-diacetoxy-2-cyclopentene.

According to the present invention, the above-mentioned alcohols (Z-OH) and the organic solvents can be used in the mobile phase.

The hydrolases usable in the fixed phase may be purified products or crude products and may be hydrolases in the form of powder or granules or cells (e.g., treated cells, pausing or resting cells) capable of forming hydrolases. Typical examples of the hydrolases are as shown before.

The hydrolases may be preferably supported on an immobilizing carrier. Examples of such carriers are polymers such as polystyrene, polypropylene, starches, and glutenes and inorganic such as activated carbon, porous glass, Celite®, zeolite, kaolinite, bentonite, alumina, silica gel, hydroxyapatite, calcium phosphate, and metallic oxides. The immobilization can be carried out by physically adsorbing on the carriers, followed by drying. The immobilization of enzymes by the physical adsorption is advantageous because the immobilization operation is easy and also because the possibility of enzyme deactivation is very small. This method is not effective in the conventional aqueous reaction because the enzyme/carrier bonding is weak when compared to the ionic bonding method and covalent bonding method and, therefore, the enzyme is easily eliminated from the carrier. However, according to the present invention, the elimination of the enzyme from the carrier is suppressed in the organic solvent due to the hydrophobicity of the organic solvent, and thus the enzyme physically adsorbed on the carrier can be advantageously used in the present invention.

In the practice of the present invention, the water content of the reaction system should be lowered so that the reaction can be effected substantially under nonaqueous conditions. However, the presence of a very small amount of water is required for enzymes, and thus the water content in a mobile phase, i.e., the reaction substrate, the alcohol, and the organic solvent is preferably 2% (w/v) or less, more preferably 0.5% (w/v) or less. On the other hand, the water content in the fixed phase, i.e., the powdered or granulated enzyme is preferably 0.1 to 10% (w/v), more preferably 0.5 to 5% (w/v). The above-mentioned water content of each substance can be adjusted by various drying methods, for example, by using an appropriate drying agent in the case of liquid or drying in a vacuum dessicator in the case of a solid.

One advantageous feature of the present invention is that a non-enzymatic decomposition reaction, i.e., the non-sterically selective reaction which causes the decrease in the optical purity due to carboxylic acid formed by ester hydrolysis, can be suppressed by reducing the water content of the reaction system to a low volume and that enzymes, which are unstable in a water-organic solvent coexistence system, can be used in a highly active state for a long time in the continuous reaction system.

Although there are no critical limitations to the mole ratio of the reaction substrate and the nucleophilic reagent, i.e., alcohol, used in the present invention, the preferable mole ratio of substrate/alcohol is 1/0.5 or more, in the case of the optical resolution and 1/1 or more.

In the practice of the present invention, the solutions of the reaction substrate and the alcohol are preferably mixed immediately before feeding to the fixed phase, i.e., the enzyme column, followed by feeding to the column as a mixture. The optimum feed rates of the substrate and the alcohol and the optimum amount of enzymes packed into the column can be easily determined by those skilled in the art, depending, for example, upon the reactivities of the reactants. Although there are no critical limitations to the reaction temperatures so long as the temperature is lower than the boiling points of the substrates, alcohols, and organic solvents, the typical reaction temperature is about 5° to 70° C.

As mentioned above, according to the present invention, an effective preparation process of intermediates for pharmaceutical products can be provided. This process can shorten the synthesis steps of the conventional synthesis method from optically active natural products such as sugars and amino acids.

Generally speaking, the optically active substances obtained from the present invention are intermediate products for the synthesis of optically active β-blocker, which is used as an agent for arrhythmia and hypotensive agent.

Heretofore, when β-blocker is prepared from natural optically active starting substances, it is believed that the method using D-mannitol is most effective. However, when D-mannitol is used as a starting material, 9 synthesis steps are required to obtain an optically active (R)-solketal and, furthermore, since a lead compound is used as a reaction agent, a safety problem with regard to the resultant reaction products may unpreferably arise.

On the other hand, according to the present invention, racemic solketal, which is extremely cheaper than D-mannitol, can be used as a starting material and only two steps (i.e., esterification and enzymatic transesterification reaction) are required for the synthesis, without using poisonous substances such as heavy metals, and optically active solketal can be prepared with a high safety.

Furthermore, in conventional methods using enzymes, optically active substances are obtained in the hydrolysis of esters of racemic aliphatic alcohols having 3 carbon atoms in an aqueous solution by using lipases. However, in this method, since expensive enzymes are dissolved in water, the recovery of the expensive enzymes is substantially impossible and, therefore, the enzymes are disposable and reutilization is impossible.

Contrary to this, according to the present invention, since the organic solvent is used, the desired reaction occurs in a condition such that the enzyme is not dissolved but is suspended in the solvent. Furthermore, since the enzyme is extremely stable when the water content is very low, the enzyme can be recovered and reutilized.

Moreover, according to the recent Klibanov report, optically active secondary alcohol is obtained from an enzymatic esterification reaction of racemic alcohols in a transesterification reaction. However, a negative report is made on primary alcohols. Contrary to this, according to the present invention, primary alcohols having a high optical purity can be obtained, even in the case of a primary alcohol, by enzymatic alcoholysis of racemic esters in a transesterification reaction. Furthermore, when secondary alcohols are used in the present invention, a further high optical purity can be obtained.

When the optically active epihalohydrin is prepared according to the present invention, the following technically remarkably advantageous effects can be obtained.

(i) As mentioned above, according to the present invention, the sterically selective enzyme reaction is carried out by alcoholysis reaction in an organic solvent in which substrates and enzymes are used similar to those conventionally used in the hydrolysis reaction in an aqueous medium. The enzymes used are not soluble in the organic solvent and, therefore, the separation and recovery of the enzymes and the resultant products can be easily effected by filtration and the recovered enzymes can be reutilized.

(ii) Since free acids are not formed in the present invention, it is not necessary to add an aqueous alkaline solution to neutralize the acid during the reaction.

(iii) After the completion of the enzymatic reaction, the resultant mixture solution containing the (R)-ester (V) and the (S)-alcohol (IV), from which the enzyme is recovered by filtration, can be used as a starting material in the subsequent step only by removing a nucleophilic reagent, i.e., Z-OH, therefrom by water-washing or distillation, without the need for an extraction operation.

(iv) To the above-mentioned mixture solution of the (R)-ester (V) and the (S)-alcohol (IV) (when the boiling point of the organic solvent is low and the organic solvent is distilled-off simultaneously with the alcohol removal, the solvent is newly added to form the solution), an aqueous alkaline solution is added and the reaction is carried out in a two-layer system, whereby the solubility of the starting material is increased and the reactivity is improved. Thus, only the (S)-alcohol (IV) is cyclized within a short time and, as a result, the (S)-epihalohydrin (VI) can be obtained. During such a short time, the (R)-ester (V) is not changed and, therefore, the selectivity of the reaction is remarkably increased. Furthermore, after the reaction, the desired product can be separated only by liquid separation and can be easily recovered.

(v) The desired (S)-epihalohydrin (VI) can be isolated from the reaction mixture by distillation and only the (R)-ester (V) remains in the residue. Accordingly, the (R)-epi-halohydrin can be derived from the (R)-ester (V) by an alkali treatment.

Furthermore, according to the present invention, a bioreactor having an extremely high productivity can be provided by stably retaining an unstable enzyme for a long time at a high activity state in the continuation reaction system without using a complicated ultrafiltration membrane or precise filtration membrane.

Furthermore, the non-enzymatic decomposition, i.e., non-sterically selective reaction substrate causing the unpreferable decrease in the optical purity, can be advantageously prevented, whereby the desired optically active substance having a high optical purity can be effectively obtained.

Therefore, according to the present invention, (R)-solketal and (R), (S)-epihalohydrin, which are useful as an intermediate for the synthesis of pharmaceutical products and which have been prepared through a long synthesis route from natural optically active substances, can be effectively prepared.

EXAMPLES

The present invention now will be further illustrated by, but is by no means limited to, the following examples.

EXAMPLE 1

To n-butanol (10 g) previously dried on a molecular sieve 3A overnight was added a butyric acid ester of racemic 2,2-dimethyl-1,3-dioxorane-4-methanol (4 g). While this solution was maintained at 25° C., lipase (Lipase 'Amano' P) (2 g) dried overnight in the presence of phosphorus pentoxide was added. The mixture was stirred at 25° C. for 110 hours and, when the butanolysis percentage reached 58%, the enzyme was separated by filtration operation. The unreacted butyric acid ester of 2,2-dimethyl-1,3-dioxorane-4-methanol was isolated from the filtrate by distillation under a reduced pressure. The ester was found to be an ester enriched in the steric configuration S with a specific optical rotation $[\alpha]_D 28 = -0.87$ (C=4.58, ethanol) and an optical purity of 59%. When the enzyme was reused, it was found to retain the same enzyme activity.

EXAMPLE 2

To a solution obtained by adding n-hexane (20 ml), previously dried on a molecular sieve 3A, to n-butanol (10 g) previously dried on a molecular sieve 3A overnight, was added butyric acid ester of racemic 2,2-dimethyl-1,3-dioxorane-4-methanol (4 g). While this solution was maintained at 25° C., lipase (Lipase 'Amano' P) (2 g) dried overnight in the presence of phosphorus pentoxide was added. The mixture was stirred at 25° C. for 110 hours and, when the butanolysis percentage reached 63%, the enzyme was separated by filtration. The unreacted butyric acid ester of 2,2-dimethyl-1,3-dioxorane-4-methanol was isolated from the filtrate by distillation under a reduced pressure. The ester was found to be an ester enriched in the steric configuration S with a specific optical rotation $[\alpha]_D 28 = -0.84$ (C=4.75, ethanol) and an optical purity of 57%. When the enzyme was reused, it was found to retain the same enzyme activity.

EXAMPLE 3

To n-butanol (30 g) previously dried on a molecular sieve 3A overnight was added butyric acid ester of racemic 2,3-epoxypropanol (2.9 g). While this solution was maintained at 25° C., lipase (Lipase 'Amano' P) (0.3 g) dried overnight in the presence of phosphorus pentoxide was added. The mixture was stirred at 25° C. for 54 hours and, when the butanolysis percentage reached 58%, the enzyme was separated by filtration. The unreacted butyric acid ester of 2,3-epoxypropanol was isolated from the filtrate by distillation under a reduced pressure. The ester was found to be an ester enriched in the steric configuration R with a specific optical rotation $[\alpha]_D 28 = -13.8$ (C=20.84, chloroform) and an optical purity of 51%. When the enzyme was reused, it was found to retain the same enzyme activity.

EXAMPLE 4

To n-butanol (10 g) previously dried on a molecular sieve 3A overnight was added butyric acid ester of racemic 2,3-dichloro-1-propanol (3.4 g). While this solution was maintained at 25° C., porcine pancreatic lipase (produced by Sigma Co.) (2 g) dried overnight in the presence of phosphorus pentoxide was added. The mixture was stirred at 25° C. for 25 hours and, when the butanolysis percentage reached 59%, the enzyme was separated by filtration. The unreacted butyric acid ester of 2,3-dichloro-1-propanol was isolated from the filtrate by distillation under a reduced pressure. The ester was found to be an ester enriched in the steric configuration S with a specific optical rotation $[\alpha]_D 28 = -9.1$ (C=1.0, methanol) and an optical purity of 55%. When the enzyme was reused, it was found to retain the same enzyme activity.

EXAMPLE 5

To n-butanol (10 g) previously dried on a molecular sieve 3A two overnight was added butyric acid ester of racemic 2,2-dimethyl-1,3-dioxorane-4-methanol (4 g). While this solution was maintained at 25° C., Talipase (produced by Tanabe Seiyaku) (2 g) dried with phosphorus pentoxide under a reduced pressure was added. The mixture was stirred at 25° C. for 100 hours and, when 60% of the ester was subjected to alcoholysis, the enzyme was separated by filtration. The unreacted butyric acid ester of 2,2-dimethyl-1,3-dioxorane-4-methanol was isolated from the filtrate by distillation. The ester was found to be optically active and gave the same results as in Example 1.

EXAMPLE 6

To racemic 2-butanol (10 g) previously dried on a molecular sieve 3A overnight was added butyric acid ester of racemic 2,2-dimethyl-1,3-dioxorane-4-methanol (4 g). While this solution was maintained at 25° C., Lipase M (produced by Amano Seiyaku) (2 g) dried with phosphorus pentoxide under a reduced pressure was added. The mixture was stirred at 25° C. for 100 hours and, when 60% of the ester was subjected to alcoholysis, the enzyme was separated by filtration. The unreacted butyric acid ester of 2,2-dimethyl-1,3-dioxorane-4-methanol was isolated from the filtrate by distillation. The ester was found to be optically active and gave the same results as in Example 5.

EXAMPLE 7

To racemic 2-butanol (10 g) previously dried on a molecular sieve 3A overnight was added butyric acid ester of racemic 2,2-dimethyl-1,3-dioxorane-4-methanol (4 g). While this solution was maintained at 25° C., Olipase (produced by Osaka Saikin Kenkyusho) (2 g) dried with phosphorus pentoxide under a reduced pressure was added. The mixture was stirred at 25° C. for 200 hours and, when 60% of the ester was subjected to alcoholysis, the enzyme was separated by filtration. The unreacted butyric acid ester of 2,2-dimethyl-1,3-dioxorane-4-methanol was isolated from the filtrate by distillation. The ester was found to be optically active and gave the same results as in Example 5.

EXAMPLE 8

To isopropanol (10 g) previously dried on a molecular sieve 3A overnight was added butyric acid ester of racemic 2,2-dimethyl-1,3-dioxorane-4-methanol (4 g). While this solution was maintained at 25° C., porcine liver esterase (produced by Sigma Co.) (0.2 g) dried with phosphorus pentoxide under a reduced pressure was added. The mixture was stirred at 25° C. for 100 hours and, when 60% of the ester was subjected to alcoholysis, the enzyme was separated by filtration. The unreacted butyric acid ester of 2,2-dimethyl-1,3-dioxorane-4-methanol was isolated from the filtrate by distillation. The ester was found to be optically active and gave the same results as in Example 5.

EXAMPLE 9

To n-propanol (10 g) previously dried on a molecular sieve 3A overnight was added butyric acid ester of racemic 2,3-epoxy-1-propanol (3.4 g). While this solution was maintained at 25° C., lipase (Lipase 'Amano' P) (2 g) dried with phosphorus pentoxide under a reduced pressure was added. The mixture was stirred at 25° C. for 50 hours and, when 60% of the ester was subjected to alcoholysis, the enzyme was separated by filtration. The unreacted butyric acid ester of 2,3-epoxypropanol was isolated from the filtrate by distillation. The ester was found to be optically active and gave the same results as in Example 3.

EXAMPLE 10

To a solution obtained by adding dichloromethane (100 ml) previously dried on a molecular sieve 4A overnight to n-butanol (4.45 g) previously dried on a molecular sieve 3A overnight was added butyric acid ester (2 g) of racemic 2,2-dimethyl-1,3-dioxorane-4-methanol. While the solution was maintained at 25° C., lipase (Lipase 'Amano' P) (20 g) dried overnight in the presence of phosphorus pentoxide was added. The mixture was stirred at 25° C. for 126 hours, and when the butanolysis percentage reached 64%, the enzyme was separated by filtration. The unreacted butyric acid ester of 2,2-dimethyl-1,3-dioxorane-4-methanol was isolated by distillation under a reduced pressure.

When the ester was analyzed by high performance liquid chromatography, the optical purity thereof was found to be 80%.

When the separated enzyme was reused, it was found to have the same enzyme activity.

EXAMPLE 11

(R,S)-3-chloro-2-acetoxy-1-p-toluenesulfonyloxypropane 3.07 g (10 mmol) was dissolved in a solution of n-hexane (80 ml) and 2-propanol (40 ml) previously dried on a molecular sieve 4A overnight or longer. Subsequently, lipase (Amano P produced by Amano Seiyaku Co.) 10 g was added to this solution, and the mixture was stirred at 25° C. at 150 rpm. After 2 hours, the enzyme powder was removed by filtration, and the solvent was evaporated from the filtrate under a reduced pressure. To the residue were added 50 ml of ether and 50 ml of 1N-NaOH aqueous solution, and the mixture was stirred under ice-cooling. After 5 minutes, the aqueous phase was removed, and the organic phase was washed twice with saturated aqueous sodium chloride, followed by drying over anhydrous magnesium sulfate. After the solution was filtered, ether was evaporated under a reduced pressure at 0° C. and the residue was distilled at 25° C. under a reduced pressure to give S-epichlorohydrin at a yield of 70% of the theoretical amount. Further, the residue was treated with 1 mol of NaOMe to obtain R-epichlorohydrin at a yield of 60% of the theoretical amount. These S- and R-epichlorohydrins were found to have optical purities of 99% or higher, as a result of a measurement of the optical rotations.

EXAMPLE 12

(R,S)-3-chloro-2-acetoxy-1-p-benzenesulfonyloxypropane 2.92 g (10 mmol) was dissolved in a solution of n-hexane (80 ml) and 2-propanol (40 ml) previously dried on a molecular sieve 4A overnight or longer. Subsequently, lipase (Amano P produced by Amano Seiyaku Co.) 10 g was added to this solution, and the mixture was stirred at 25° C. at 150 rpm. After 2 hours, the enzyme powder was removed by filtration, and the solvent was evaporated from the filtrate under a reduced pressure. To the residue were added 50 ml of ether and 50 ml of 1N-NaOH aqueous solution, and the mixture was stirred under ice-cooling. After 5 minutes, the aqueous phase was removed, and the organic phase was washed twice with saturated aqueous sodium chloride, followed by drying over anhydrous magnesium sulfate. After the solution was filtered, ether was evaporated under a reduced pressure at 0° C. and the residue was distilled at 25° C. under a reduced pressure to give S-epichlorohydrin at a yield of 62% of the theoretical amount. Further, the residue was treated with 1 mol of NaOMe to obtain R-epichlorohydrin at a yield of 58% of the theoretical amount. These S- and R-epichlorohydrins were found to have optical purities of 99% or higher, as a result of a measurement of the optical rotations.

EXAMPLE 13

(R,S)-3-chloro-2-acetoxy-1-trifluoromethanesulfonyloxypropane 2.85 g (10 mmol) was dissolved in a solution of n-hexane (80 ml) and 2-propanol (40 ml) previously dried on a molecular sieve 4A overnight or longer. Subsequently, lipase (Amano P produced by Amano Seiyaku Co.) 10 g was added to this solution, and the mixture was stirred at 25° C. at 150 rpm. After 2 hours, the enzyme powder was removed by filtration, and the solvent was evaporated from the filtrate under a reduced pressure. To the residue were added 50 ml of ether and 50 ml of 1N-NaOH aqueous solution, and the mixture was stirred under ice-cooling. After 5 minutes, the aqueous phase was removed, and the organic phase was washed twice with saturated aqueous sodium chloride, followed by drying over anhydrous magnesium sulfate. After the solution was filtered, ether was evaporated under a reduced pressure at 0° C. and the residue was distilled at 25° C. under a reduced pressure to give S-epichlorohydrin at a yield of 62% of the theoretical amount. Further, the residue was treated with 1 mol of NaOMe to obtain R-epichlorohydrin at a yield of 60% of the theoretical amount. These S- and R-epichlorohydrins were found to have optical purities of 90% or higher, as a result of a measurement of the optical rotations.

EXAMPLE 14

(R,S)-3-chloro-2-acetoxy-1-methanesulfonyloxypropane 2.31 g (10 mmol) was dissolved in a solution of n-hexane (80 ml) and 2-propanol (40 ml) previously dried on a molecular sieve 4A overnight or longer. Subsequently, lipase (Amano P produced by Amano Seiyaku Co.) 10 g was added to this solution, and the mixture was stirred at 25° C. at 150 rpm. After 2 hours, the enzyme powder was removed by filtration, and the solvent was evaporated from the filtrate under a reduced pressure. To the residue were added 50 ml of ether and 50 ml of 1N-NaOH aqueous solution, and the mixture was stirred under ice-cooling. After 5 minutes, the aqueous phase was removed, and the organic phase was washed twice with saturated aqueous sodium chloride, followed by drying over anhydrous magnesium sulfate. After the solution was filtered, ether was evaporated under a reduced pressure at 0° C. and the residue was distilled at 25° C. under a reduced pressure to give S-epichlorohydrin at a yield of 63% of the theoretical amount. Further, the residue was treated with 1 mol of NaOMe to obtain R-epichlorohydrin at a yield of 61% of the theoretical amount. These S- and R-epichlorohydrins were found to have optical purities of 60% and 50%, respectively, as a result of a measurement of the optical rotations.

EXAMPLE 15

(R,S)-3-chloro-2-acetoxy-1-p-toluenesulfonyloxypropane 3.07 g (10 mmol) was dissolved in a solution of benzene (80 ml) and 2-propanol (20 ml) previously dried on a molecular sieve 4A overnight or longer. Subsequently, lipase (Amano P produced by Amano Seiyaku Co.) 10 g was added to this solution, and the mixture was stirred at 25° C. at 150 rpm. After 24 hours, the enzyme powder was removed by filtration, and the solvent was evaporated from the filtrate under a reduced pressure. To the residue were added 50 ml of dichloromethane and 50 ml of 1N-NaOH aqueous solution, and the mixture was stirred under ice-cooling. After 5 minutes, the aqueous phase was removed, and the organic phase was washed twice with saturated aqueous sodium chloride, followed by drying over anhydrous magnesium sulfate. After the solution was filtered, dichloromethane was evaporated under a reduced pressure at 0° C. and the residue was distilled at 25° C. under a reduced pressure to give S-epichlorohydrin at a yield of 58% of the theoretical amount. Further, the residue was treated with 1 mol of NaOMe to obtain R-epichlorohydrin at a yield of 60% of the theoretical amount. These S- and R-epichlorohydrins were found to have optical purities of 99% or higher, as a result of a measurement of the optical rotations.

EXAMPLE 16

(R,S)-3-chloro-2-acetoxy-1-p-toluenesulfonyloxypropane 3.07 g (10 mmol) was dissolved in a solution of dichloromethane (80 ml) and 2-propanol (20 ml) previously dried on a molecular sieve 4A overnight or longer. Subsequently, lipase (Amano P produced by Amano Seiyaku Co.) 10 g was added to this solution, and the mixture was stirred at 25° C. at 150 rpm. After 120 hours, the enzyme powder was removed by filtration, and the solvent was evaporated from the filtrate under a reduced pressure. To the residue were added 50 ml of ether and 50 ml of 1N-NaOH aqueous solution, and the mixture was stirred under ice-cooling. After 5 minutes, the aqueous phase was removed, and the organic phase was washed twice with saturated aqueous sodium chloride, followed by drying over anhydrous magnesium sulfate. After the solution was filtered, ether was evaporated under a reduced pressure at 0° C. and the residue was distilled at 25° C. under a reduced pressure to give S-epichlorohydrin at a yield of 55% of the theoretical amount. Further, the residue was treated with 1 mol of NaOMe to obtain R-epichlorohydrin at a yield of 58% of the theoretical amount. These S- and R-epichlorohydrins were found to have optical purities of 99% or higher, as a result of a measurement of the optical rotations.

EXAMPLE 17

(R,S)-3-chloro-2-acetoxy-1-p-toluenesulfonyloxypropane 3.07 g (10 mmol) was dissolved in a solution of dichloromethane (80 ml) and 2-propanol (20 ml) previously dried on a molecular sieve 4A overnight or longer. Subsequently, lipase (CES produced by Amano Seiyaku Co.) 10 g was added to this solution, and the mixture was stirred at 25° C. at 150 rpm. After 120 hours, the enzyme powder was removed by filtration, and the solvent was evaporated from the filtrate under a reduced pressure. To the residue were added 50 ml of ether and 50 ml of 1N-NaOH aqueous solution, and the mixture was stirred under ice-cooling. After 5 minutes, the aqueous phase was removed, and the organic phase was washed twice with saturated aqueous sodium chloride, followed by drying over anhydrous magnesium sulfate. After the solution was filtered, ether was evaporated under a reduced pressure at 0° C. and the residue was distilled at 25° C. under a reduced pressure to give S-epichlorohydrin at a yield of 65% of the theoretical amount. Further, the residue was treated with 1 mol of NaOMe to obtain R-epichlorohydrin at a yield of 59% of the theoretical amount. These S- and R-epichlorohydrins were found to have optical purities of 99% or higher, as a result of a measurement of the optical rotations.

EXAMPLE 18

(R,S)-3-chloro-2-acetoxy-1-p-toluenesulfonyloxypropane 3.07 g (10 mmol) was dissolved in a solution of dichloromethane (80 ml) and 2-propanol (20 ml) previously dried on a molecular sieve 4A overnight or longer. Subsequently, lipase (porcine pancreatic lipase, produced by Sigma Co.) 10 g was added to this solution, and the mixture was stirred at 25° C. at 150 rpm. After 120 hours, the enzyme powder was removed by filtration, and the solvent was evaporated from the filtrate under a reduced pressure. To the residue were added 50 ml of ether and 50 ml of 1N-NaOH aqueous solution, and the mixture was stirred under ice-cooling. After 5 minutes, the aqueous phase was removed, and the organic phase was washed twice with saturated aqueous sodium chloride, followed by drying over anhydrous magnesium sulfate. After the solution was filtered, ether was evaporated under a reduced pressure at 0° C. and the residue was distilled at 25° C. under a reduced pressure to give S-epichlorohydrin at a yield of 58% of the theoretical amount. Further, the residue was treated with 1 mol of NaOMe to obtain R-epichlorohydrin at a yield of 62% of the theoretical amount. These S- and R-epichlorohydrins were found to have optical purities of 90% and 85%, respectively, for S-isomer and R-isomer, as a result of a measurement of the optical rotations.

EXAMPLE 19

(R,S)-3-chloro-2-butanoyloxy-1-p-toluenesulfonyloxypropane 3.35 g (10 mmol) was dissolved in a solution of n-hexane (80 ml) and 2-propanol (40 ml) previously dried on a molecular sieve 4A overnight or longer. Subsequently, lipase (Amano P produced by Amano Seiyaku Co.) 10 g was added to this solution, and the mixture was stirred at 25° C. at 150 rpm. After 2 hours, the enzyme powder was removed by filtration, and the solvent was evaporated from the filtrate under a reduced pressure. To the residue were added 50 ml of dichloromethane and 50 ml of 1N-NaOH aqueous solution, and the mixture was stirred under ice-cooling. After 5 minutes, the aqueous phase was removed, and the organic phase was washed twice with saturated aqueous sodium chloride, followed by drying over anhydrous magnesium sulfate. After the solution was filtered, dichloromethane was evaporated under a reduced pressure at 0° C. and the residue was distilled at 25° C. under a reduced pressure to give S-epichlorohydrin at a yield of 61% of the theoretical amount. Further, the residue was treated with 1 mol of NaOMe to obtain R-epichlorohydrin at a yield of 62% of the theoretical amount. These S- and R-epichlorohydrins were found to have optical purities of 99% or higher, as a result of a measurement of the optical rotations.

EXAMPLE 20

In an investigation into the possibility of a reutilization of the enzyme, the enzyme powder used in Example 11 was repeatedly used. The content of the experiment repeated was conducted under entirely the same conditions as in Example 11, and the enzyme powder was washed after completion of the reaction before reutilization. After the enzyme reaction for the second time, the optical purities of S-epichlorohydrin and R-epichlorohydrin obtained by alkali treatment were found to be 99% or higher, as a result of a measurement of the optical rotations.

Further, by use of the same enzyme powder, the third enzymatic reaction was conducted and the products were subjected to alkali treatment. As a result, the optical purities of S-epichlorohydrin and R-epichlorohydrin were found to be 99% or higher.

EXAMPLE 21

A tapered glass column with an inner diameter of 40 mm and a length of 300 mm was packed with commercially available lipase "Amano P" (produced by Amano Seiyaku) (enzyme amount 220 g). The column was then connected to a pump and dipped in a water bath at 35° C. to stabilize the column temperature. A methylene dichloride solution containing racemic solketal butyric acid ester dissolved at a concentration of 50 mM (tank A) and a methylene dichloride solution containing n-butyl alcohol dissolved at a concentration of 50 mM (tank B) were each injected into the column at a flow rate of 0.5 ml per minute; these were passed through the pump and were mixed for the first time immediately before entering the column. From the methylene dichloride solution eluted from the column, undecomposed (S)-solketal butyric acid ester was obtained at an optical purity of 85%. Also, the alcoholysis percentate at this time was found to be 60%. These optical purity and alcoholysis percentages were maintained even after continuous running for 30 days.

EXAMPLE 22

A flange system glass column with an inner diameter of 23 mm and a length of 250 mm was packed with commercially available lipase "Amano P" (produced by Amano Seiyaku) (enzyme amount 100 g). The column was then connected to a pump and the column temperature was stabilized in a thermostat tank at 22° C. A toluene solution containing racemic 3-chloro-2-acetoxy-1-p-toluenesulfonyloxypropane dissolved at a concentration of 20 mM (tank A) and a toluene solution containing 2-propanol dissolved at a concentration of 25 mM (tank B) were each injected into the column at a flow rate of 0.25 ml per minute. The solutions from the tank A and the tank B were passed through the pump and mixed for the first time immediately before entering the column. From the toluene solution eluted from the column, undecomposed (R)-3-chloro-2-acetoxy-1-p-toluene-sulfonyloxypropane and (S)-3-chloro-1-p-toluene-sulfonyloxy-2-propanol were each obtained at an optical purity of 99% or higher and at a yield of 50%, which optical purity and decomposition percentages were maintained even after continuous running for 30 days.

EXAMPLE 23

A flange system glass column with an inner diameter of 23 mm and a length of 250 mm was packed with commercially available lipase "Amano P" (produced by Amano Seiyaku) (enzyme amount 100 g). The column was connected to a pump and the column temperature was stabilized in a thermostat tank at 22° C. A benzene solution containing racemic 3-chloro-2-acetoxy-1-p-toluenesulfonyloxypropane dissolved at a concentration of 20 mM (tank A) and a benzene solution containing 2-propanol dissolved at a concentration of 25 mM (tank B) were each injected into the column at a flow rate of 0.25 ml per minute. The solutions from the tank A and the tank B were passed through the pump and mixed for the first time immediately before entering the column. From the benzene solution eluted from the column, undecomposed (R)-3-chloro-2-acetoxy-1-p-toluenesulfonyloxypropane and (S)-3-chloro-1-p-toluenesulfonyloxy-2-propanol were each obtained at an optical purity of 99% or higher and at a yield of 50%, which optical purity and decomposition percentages were maintained even after continuous running for 30 days.

EXAMPLE 24

Alcoholysis reaction was conducted under the same conditions as in Example 21, except for using porcine pancreatic lipase (produced by Sigma Co.) as the lipase and racemic 2,3-dichloro-1-propanol butyric acid ester as the substrate to obtain undecomposed (S)-2,3-dichloro-1-propanol butyric acid ester and (R)-2,3-dichloropropanol.

EXAMPLE 25

Alcoholysis reaction was conducted in the same manner as in Example 22, except for using Amano P (produced by Amano Seiyaku) as the lipase and 1,3-diacetoxy-2-phenylpropane as the substrate to obtain optically active 3-acetoxy-2-phenylpropanol.

EXAMPLE 26

Alcoholysis was conducted in the same manner as in Example 22, except for using Amano P (produced by Amano Seiyaku) as the lipase and cis-1,4-diacetoxy-2-cyclopentene as the substrate to obtain optically active 4-acetoxy-2-cyclopentenol.

COMPARATIVE EXAMPLE 1

To 100 ml of 0.1 M phosphate buffer (pH 7.0) were added 20 g of the substrate (R,S)-3-chloro-2-acetoxy-1-p-toluenesulfonyloxypropane and 0.2 g of lipoprotein lipase (Amano 3), and while adjusting the pH to 7.0 with 2.5 M NaOH, an asymmetric hydrolysis reaction was carried out under stirring at 30° C. for 24 hours. The reaction mixture (200 ml) was extracted with methylene chloride, dried and concentrated under reduced pressure, followed by separation by silica gel chromatography, to obtain 8.5 g of (R)-3-chloro-2-acetoxy-1-p-toluenesulfonyloxypropane and 7.4 g of (S)-3-chloro-1-p-toluenesulfonyloxy-2-propanol. The specific optical rotations of the respective compounds were measured and found to be $[\alpha]_D 20° -9.2°$ (C=5.0, MeOH) and $[\alpha]_D 20° -2.2°$ (C=5.0 MeOH). Also, when the optical purities were measured by HPLC, both exhibited values of 99% or higher.

However, in this method, it is impossible to carry out the reaction as a continuous process, because enzyme is dissolved in the water, and because the reaction must be carried out while neutralizing free carboxylic acid formed.

We claim:

1. A process for separating an optically active substance, comprising the steps of:
   (a) effecting a transesterification reaction substantially under non-aqueous conditions between
      (i) an ester of a linear or branched aliphatic racemic alcohol selected from the group consisting of esters of primary alcohols of formula (I)

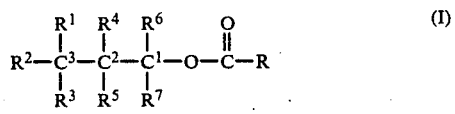

and esters of secondary alcohols of formula (II)

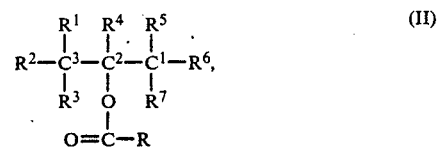

wherein $R^1$ to $R^7$ each independently represents a functional group containing at least one atom selected from the group consisting of hydrogen, carbon, a halogen, oxygen, nitrogen, sulfur and phosphorus, and R represents an aliphatic hydrocarbon residue having from 1 to 8 carbon atoms, wherein an asymmetric carbon is present only at the $C^2$ position and the carbon atoms $C^1$ and $C^3$ are not asymmetric, and
      (ii) an alcohol in an organic solvent containing a hydrolase enzyme suspended therein, said alcohol selected from the group consisting of alcohols having no asymmetric carbons atoms, racemic alcohols having at least one asymmetric carbon, and optically active alcohols,
   to form a resultant reaction mixture of the above-reacted components; and
   (b) separating an optically active compound from the reaction mixture.

2. A process as recited in claim 1, wherein the formula (I) at least two groups of $R^1$ to $R^3$ are the same and $R^6$ and $R^7$ are the same, and in formula (II) at least two groups of $R^1$ to $R^3$ are the same and at least two groups of $R^5$ to $R^7$ are the same.

3. A process as recited in claim 1, wherein the enzyme includes at least one member selected from the group consisting of lipases derived from swine pancreas, lipases derived from yeast belonging to the genus Candida, lipases derived from microorganisms belonging to a genus chosen from the group consisting of Aspergillus, Mucor and Pseudomonas, esterases derived from swine liver, and proteinases.

4. A process as recited in claim 1, wherein said organic solvent is a waterless organic solvent capable of suspending the enzyme therein.

5. A process as recited in claim 1, wherein said alcohol in the organic solvent is a linear or branched aliphatic alcohol having 1 to 10 carbon atoms, 6. A process as recited in claim 1, wherein the water content of the reaction substantially under non-aqueous conditions is 0.5 percent (w/v) or less.

7. A process according to claim 1, wherein in formula (I) $R^1$ to $R^7$ each independently represents a functional group selected from the group consisting of hydrogen, a halogen and a lower alkyl group, or two adjacent groups $R^1$ to $R^7$ together form oxygen or

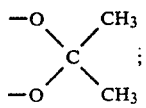

and in formula (II) $R^1$ to $R^7$ each independently represents a functional group selected from the group consisting of hydrogen, a halogen and a sulfonyloxy group.

8. A process according to claim 7, wherein in formula (I) $R^1$, $R^2$, $R^4$, $R^6$ and $R^7$ each independently represents hydrogen, and $R^3$ and $R^5$ each independently represents a halogen or together form oxygen or

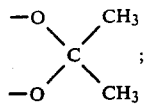

and in formula (II) $R^1$, $R^2$, $R^3$, $R^4$, $R^5$ and $R^7$ each independently represents hydrogen or a halogen, and $R^6$ represents a sulfonyloxy group.

9. A process according to claim 8, wherein said sulfonyloxy group is selected from the group consisting of

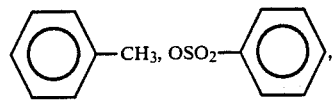

$OSO_2CF_3$ and $OSO_2CH_3$.

10. A process according to claim 9, wherein said sulfonyloxy group is p-toluenesulfonyloxy.

11. A process according to claim 8, wherein said ester is an ester of formula (I) selected from the group consisting of 2,2-dimethyl-1,3-dioxorane-4-methanol, 2,3-epoxypropanol and 2,3-dichloro-1-propanol.

12. A process according to claim 8, wherein said ester is an ester of formula (II) selected from the group consisting of 3-chloro-2-acetoxy-1-p-toluenesulfonyloxypropane, 3-chloro-2-acetoxy-1-benzenesulfonyloxypropane, 3-chloro-2-acetoxy-1-trifluoromethanesulfonyloxypropane and 3-chloro-2-acetoxy-1-methanesulfonyloxypropane.

* * * * *